United States Patent
Akintoye et al.

(10) Patent No.: US 11,419,358 B2
(45) Date of Patent: Aug. 23, 2022

(54) EDIBLE FUNGUS

(71) Applicant: Marlow Foods Limited, Stokesley (GB)

(72) Inventors: Olumyiwa A. Akintoye, Guisborough (GB); Alexander J. E. Evans, Darlington (GB)

(73) Assignee: MARLOW FOODS LIMITED, Stokesley (GB)

( * ) Notice: Subject to any disclaimer, the term of this patent is extended or adjusted under 35 U.S.C. 154(b) by 326 days.

(21) Appl. No.: 16/684,868

(22) Filed: Nov. 15, 2019

(65) Prior Publication Data

US 2020/0154752 A1 May 21, 2020

(30) Foreign Application Priority Data

Nov. 19, 2018 (GB) ...................................... 1818800

(51) Int. Cl.
*A23L 31/00* (2016.01)
*A23L 3/36* (2006.01)

(52) U.S. Cl.
CPC .................. *A23L 31/00* (2016.08); *A23L 3/36* (2013.01)

(58) Field of Classification Search
CPC .................................. A23L 31/00; A23L 3/36
USPC .......................................................... 426/61
See application file for complete search history.

(56) References Cited

U.S. PATENT DOCUMENTS

2004/0185162 A1* 9/2004 Finnigan .............. A23D 7/0056
426/615

FOREIGN PATENT DOCUMENTS

| GB | 2518726 A | 4/2015 |
|---|---|---|
| GB | 2563379 A | 12/2018 |
| WO | 1995023843 A1 | 9/1995 |
| WO | 1996021362 A1 | 7/1996 |
| WO | 2000015045 A1 | 3/2000 |
| WO | 2018002587 A1 | 1/2008 |
| WO | 2016120594 A1 | 8/2016 |

OTHER PUBLICATIONS

Wiebe, "Myco-protein from Fusarium venenatum: a well-established product for human consumption", Applied Microbiology and Biotechnology, vol. 58, 2002, pp. 421-427.
Mousavi et al., "A Novel Technique for Ice Crystal Visualization in Frozen Solids Using X-Ray Micro-Computed Tomography", Journal of Food Science, vol. 70, 2005, pp. E437-E442.
GB Search Report for GB1818800.3, dated Jul. 24, 2019 (2 pages).

* cited by examiner

*Primary Examiner* — Brent T O'Hern
(74) *Attorney, Agent, or Firm* — Shumaker, Loop & Kendrick, LLP

(57) ABSTRACT

An elongate product comprises a filamentous fungus wherein the product has a dimension (A) measured in a first direction and a dimension (B) measured in a second direction, wherein dimension (A) is in the range 2 mm to 15 mm and dimension (B) is in the range 10 mm to 50 mm. The product is frozen mechanically in a relatively short time to produce ice-crystal sizes within the product of less than 20.0 μm, s. The product has a very long shelf life and when defrosted is found to perform like fresh paste when mixed with other ingredients.

20 Claims, 3 Drawing Sheets

EDIBLE FUNGUS

TECHNICAL FIELD AND BACKGROUND

This invention relates to edible fungus and particularly, although not exclusively, relates to edible fungus in the form of a filamentous fungus. In a preferred embodiment, the edible fungus is used, suitably after being mixed with other ingredients, in a foodstuff as a meat substitute.

It is desirable to be able to store filamentous fungus prior to incorporation into foodstuffs. This would allow the filamentous fungus to be transported long distances from the place of manufacture to another place where the filamentous fungus may be used to produce a foodstuff; and would allow excess filamentous fungus produced in a fermentation plant to be stored until needed. However, storage of filamentous fungus which subsequently needs to be texturized to produce an edible foodstuff is not trivial.

Less than optimum storage can be detrimental to the production and eating quality of a foodstuff incorporating previously stored material.

Although not publicly disclosed, filamentous fungus may be treated for storage on an industrial scale by use of air blast freezing. In the process, air at a temperature between −18° C. and −34° C. is passed through a tunnel in which a belt carrying discs of dimensions of 10 mm thickness and 45 mm diameter and a weight of about 17 g after freezing are also passed. During such passage, the filamentous fungus becomes frozen and, thereafter, it can be stored at −18° C. to −25° C. in a commercial/industrial cold storage unit until it is needed in the preparation of a foodstuff. The aforementioned process works well and allows the filamentous fungus to be stored for three to four months before being incorporated into a foodstuff. However, longer term storage can lead to problems downstream. In particular, Applicant has found that, after three to four months storage of filamentous fungus frozen as described, it is difficult to disperse defrosted filamentous fungus into foodstuffs using industrial mixers. Although not wishing to be bound by theory, this is believed to be due to filaments and/or bundles of filaments of the edible fungus becoming welded together; such welded filaments are found not to readily separated making dispersion of the filaments difficult. It is found that, if such defrosted material is used in foodstuffs, there is a risk that foodstuffs produced may not be properly mixed, leading to production of foodstuffs which are not homogenous and/or which have undesirable rheological properties. Since such foodstuffs are likely to be unacceptable to consumers, Applicant regards the maximum time filamentous fungus of the type described can be stored prior to incorporation into foodstuffs to be three to four months.

It should also be appreciated that any method used to freeze filamentous fungus must not detrimentally affect downstream processing, for example freeze texturization, of the filamentous fungus with other ingredients to define a foodstuff which has appropriate mouth feel (e.g. a fibrous texture and juiciness on chewing) which is acceptable to consumers. It is known, for example from WO 00/15045 (DSM), WO96/21362 (Zeneca) and WO95/23843 (Zeneca) to use edible filamentous fungi as a meat-substitute, for example in the preparation of burgers and sausages. In such uses, filaments of the fungi are bound together, for example with egg albumin and are texturized so the product resembles muscle fibres and therefore has a meat-like appearance and texture. Meat substitutes of the type described have been widely commercially available for many years under the trade mark QUORN.

It will be appreciated that freeze texturization of products incorporating filamentous fungus involves a carefully controlled process. The texturization aims to affect the fungus so it produces a texture similar to animal muscle meat texture. To mimic natural meat texture, a foodstuff incorporating filamentous fungus should ideally satisfy two major aspects of natural meat texture—firstly, it should have a fibrous texture on chewing; and, secondly, it should release liquid (i.e. be juicy) on chewing. Freeze texturization is found to advantageously produce the aforementioned aspects of natural meat in foodstuffs incorporating filamentous fungus. Thus, it should be appreciated that, in freeze texturization, the tendency for filaments of filamentous fungus to become welded after freezing may be used to provide an advantageous effect.

Figure 1:
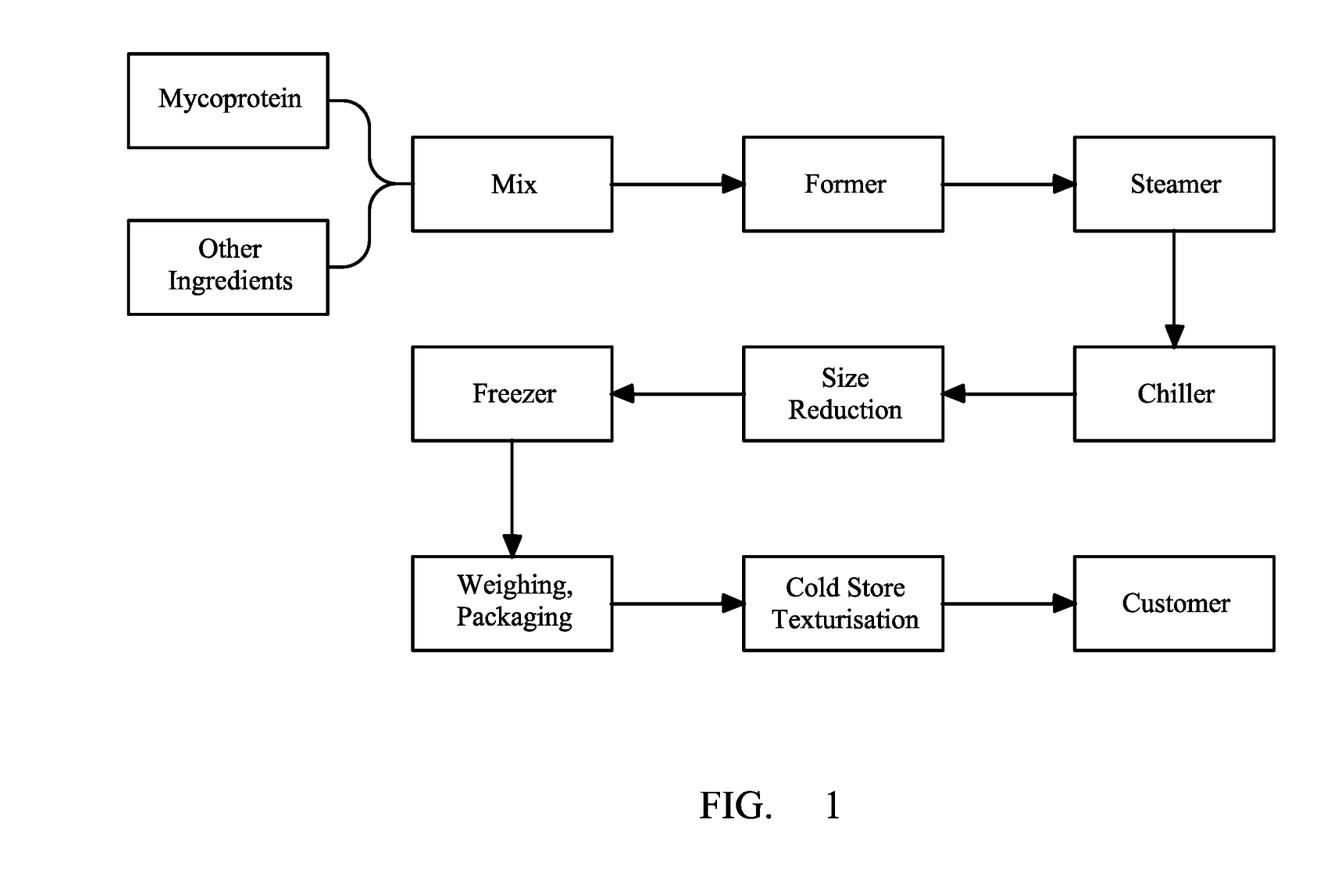
FIG. 1 is a schematic representation of steps, including a freeze texturization step, in the production of mycoprotein-containing products for human consumption.

FIG. 1 provides an overview of process steps taken to prepare a foodstuff containing filamentous fungus in the form of a mycoprotein as hereinafter referred to. In the process, mycoprotein (the fungus product of a fermentation process after RNA reduction and dewatering by centrifugation to approximately 25 wt % solids content) is mixed with other ingredients it is desired to incorporate to produce a substantially homogenous mass of a mycoprotein-containing foodstuff (for example mince, burgers, pieces/strips). The homogenous mass is put through a former and then a steamer (e.g. over 87° C. for 25-30 minutes). The steamed product is then chilled (e.g. −5 to −10° C. for about 20 minutes) which improves the texture of the product by making it slightly firmer. There follows an optional size reduction process followed by a second texturization step involving freezing. Thereafter, products are weighed and packaged prior to the final texturization step at −18° C. in a cold store for at least 7 days. This final freeze texturization step is essential, since the freezing process tends to weld the filaments of the fungus together to significantly improve rheological properties of the foodstuff. After texturization, products can be delivered to retail outlets for sale to customers.

Without the final texturization step described, the rheological properties (e.g. firmness, fibrosity, succulence, bittiness, pulpiness etc) of the foodstuff may be unacceptable.

Thus, it will be appreciated that freezing filamentous fungus, such as mycoprotein incorporated as an ingredient in a foodstuff can, in some circumstances (e.g. in freeze texturization), have desirable effects. However, it is desirable in the context of storage of mycoprotein (in a substantially pure form and in the absence of other ingredients) that the stored mycoprotein is, after being defrosted, substantially rheologically identical to fresh mycoprotein paste (i.e. mycoprotein paste which has never been frozen). In reality, it has been difficult to produce mycoprotein paste which can be stored for long periods (e.g. in excess of four months and suitably up to several years) and which can be downstream processed in substantially the same manner as fresh paste to produce foodstuffs incorporating the paste with other ingredients. Thus, there is a dilemma: it is believed to be desirable when freezing pure mycoprotein for storage to avoid welding of filaments; but it is believed desirable for such welding to take place in freeze texturization of foodstuffs incorporating mycoprotein. Whilst additives have been considered by Applicant in an attempt to reduce welding of filaments of mycoprotein on freezing of the mycoprotein for storage, it is found that such additives are detrimental to any subsequent freeze texturization process in the final foodstuff.

Applicant's co-pending application No. GB 1707876.7 discloses cryogenic freezing of mycoprotein paste to provide paste having a store life of more than a year. Whilst the process works well, capital costs of equipment are high and it is costly to operate.

SUMMARY

It is an object of the invention to address the aforementioned problems.

It is also an object of preferred embodiments of the present invention to extend the maximum storage time of filamentous fungus whilst maintaining the ability to readily disperse the fungus with other ingredients in making a foodstuff in a cost-effective manner.

BRIEF DESCRIPTION OF THE DRAWINGS

Specific embodiments of the invention will now be described, by way of example, with reference to the accompanying drawings, in which.

DETAILED DESCRIPTION

According to a first aspect of the invention, there is provided a product comprising a filamentous fungus wherein the product has a dimension (A) measured in a first direction and a dimension (B) measured in a second direction, wherein dimension (A) is in the range 2 mm to 15 mm and dimension (B) is in the range 10 mm to 50 mm.

Preferably dimension (B) is greater than dimension (A).

Dimension (A) is suitably at least 3 mm, is preferably at least 4 mm, is more preferably at least 5 mm and, especially, is at least 6 mm. It may be less than 13 mm, suitably less than 12 mm, preferably less than 10 mm, more preferably less than 9 mm, especially 8 mm or less. In some cases, the dimension (A) may be less than 5 mm for example in the range 2 to 4 mm.

Dimension (B) is suitably at least 12 mm, is preferably at least 14 mm, is more preferably at least 16 mm and, especially, is at least 18 mm. It may be less than 40 mm, suitably less than 30 mm, preferably less than 28 mm, more preferably less than 26 mm, especially 23 mm or less.

Said product is preferably elongate, suitably in said second direction. It may comprise an extrudate. It may have a substantially constant cross-sectional area along substantially its entire extent. It preferably has a substantially constant cross-section in said second direction. It may have a substantially constant cross-sectional shape along substantially its entire extent. It may have a substantially constant cross-sectional shape in said second direction. The cross-sectional shape (e.g. said cross-sectional shape which is substantially constant in said second direction) preferably includes at least one line of symmetry. Preferably, it includes two lines of symmetry.

Said cross-sectional shape (e.g. said cross-sectional shape which is substantially constant in said second direction) is preferably not polygonal. Said cross-sectional shape (e.g. said cross-sectional shape which is substantially constant in said second direction) preferably includes a curved surface; it preferably includes a single endless curved surface. Said cross-sectional shape (e.g. said cross-sectional shape which is substantially constant in said second direction) is preferably substantially circular or oval shaped. More preferably, it is substantially circular.

Said product may have a cross-sectional area (which is preferably curved, for example circular) of less than 175 $mm^2$, suitably less than 150 $mm^2$, preferably less than 125 $mm^2$, more preferably less than 100 $mm^2$, especially less than 90 $mm^2$. Said cross-sectional area may be at least 5 $mm^2$. In some embodiments, it may be at least 20 $mm^2$, preferably at least 40 $mm^2$, more preferably at least 60 $mm^2$, especially at least 70 $mm^2$.

Dimension (A) suitably refers to the maximum dimension of said cross-sectional area. It preferably refers to the maximum diameter of the product. Dimension (A) is preferably substantially constant along the elongate extent of said product. Dimension (A) is preferably substantially constant for substantially all diameters of the product measured across the product, substantially perpendicular to the second direction.

Preferably, said product has a ratio defined as the surface area (in $mm^2$) divided by the volume (in $mm^3$) of at least 0.3 $mm^{-1}$, more preferably at least 0.4 $mm^{-1}$. Said ratio may be less than 5 $mm^{-1}$, or less than 2.5 $mm^{-1}$. Said ratio may be, in the range 0.35 $mm^{-1}$ to 2.5 $mm^{-1}$.

Dimension (B) suitably refers to the maximum dimension of the product. It suitably refers to the length of the product. The product is preferably elongate in the direction of dimension (B). In a preferred embodiment, a substantially elongate axis of the product extends in said second direction, and preferably, said curved surface (e.g. a cylindrical wall) of the product extends around said elongate axis.

In a preferred embodiment, said product includes opposing ends which are spaced apart in said first direction. The ends suitably face in substantially opposite directions. Said ends are preferably spaced apart by a wall (e.g. comprising a curved surface) of the product which extends around said substantially elongate axis. Said ends may have a cross-sectional area (which is preferably curved, for example circular) of less than 175 $mm^2$, suitably less than 150 $mm^2$, preferably less than 125 $mm^2$, more preferably less than 100 $mm^2$, especially less than 90 $mm^2$. Said cross-sectional area may be at least 5 $mm^2$. In some embodiments, it may be at least 20 $mm^2$, preferably at least 40 $mm^2$, more preferably at least 60 $mm^2$, especially at least 70 $mm^2$.

The aspect ratio of the product is defined as the dimension (B) divided by dimension (A). Said aspect ratio may be at least 1, preferably at least 1.2, more preferably at least 1.5. Said aspect ratio may be less than 10, suitably less than 8, preferably less than 6, more preferably less than 4, especially less than 3.

Said product is preferably in the form of a rod as described herein. Given the way the rod is made, it may have an elongate extent which may not necessarily be geometrically straight—for example, it may curve slightly. Additionally, opposing ends of the rod may be substantially planar and/or flat (e.g. if they are produced by cutting an extrudate) or may be jagged, if they are formed by being broken from an extrudate.

Said product may be in a frozen state. It may be at a temperature of less than $-10°$ C., preferably less than $-15°$ C., more preferably less than $-17°$ C. The temperature may be at least $-25°$ C., for example at least $-22°$ C.

The ice-crystal size (eg preferably the average ice-crystal size) within the product may be less than 20.0 µm, suitably less than 10.0 µm, preferably less than 5.0 µm, for example less than 3.5 µm when assessed as described herein. The average ice-crystal size may be greater than 0.5 µm or greater than 1 µm.

Said filamentous fungus suitably comprises particles of said filamentous fungus. Said filamentous fungus preferably comprises fungal mycelia and suitably at least 80 wt %, preferably at least 90 wt %, more preferably at least 95 wt % and, especially, at least 99 wt % of the fungal particles in said foodstuff comprise fungal mycelia. Some filamentous fungi may include both fungal mycelia and fruiting bodies. Said filamentous fungus preferably comprise a filamentous fungus of a type which does not produce fruiting bodies. Where, however, a filamentous fungus of a type which produces fruiting bodies is used, the fungal particles in said product suitably include at least 80 wt %, preferably at least 90 wt %, more preferably at least 95 wt % of fungal mycelia. Preferably, said fungal particles comprise substantially only fungal mycelia—that is, fungal particles in said product preferably do not include any fruiting bodies.

Preferred fungi for said fungal particles have a cell wall which includes chitin and/or chitosan. Preferred fungi have a cell wall which includes polymeric glucosamine. Preferred fungi have a cell wall which includes β1-3 and 1-6 glucans.

Said filamentous fungus preferably comprises fungus selected from fungi imperfecti.

Preferably, said filamentous fungus comprises, and preferably consists essentially of, cells of *Fusarium* species, especially of *Fusarium venenatum* A3/5 (formerly classified as *Fusarium graminearum*) (IMI 145425; ATCC PTA-2684 deposited with the American Type Culture Collection, 10801 University Boulevard, Manassas, Va.) as described for example in WO96/21361 (Zeneca) and WO95/23843 (Zeneca).

Preferably, said filamentous fungus is non-viable. Preferably, said filamentous fungus has been treated to lower the level of RNA in the fungus. Thus, the level of RNA in the filamentous fungus used is preferably less than the level in an identical fungus when in a viable state. The level of RNA in the filamentous fungus is preferably less than 2 wt % on a dry matter basis.

Particles of said filamentous fungus in said product may comprise filaments having lengths of less than 1000 µm, preferably less than 800 µm. Said filaments may have a length greater than 100 µm, preferably greater than 200 µm. Preferably, fewer than 5 wt %, preferably substantially no, fungal particles in said product have lengths of greater than 5000 µm; and preferably fewer than 5 wt %, preferably substantially no, fungal particles have lengths of greater than 2500 µm. Preferably, values for the number average of the lengths of said fungal particles in said product are also as stated above.

Particles of said filamentous fungus in said product may comprise filaments having diameters of less than 20 µm, preferably less than 10 µm, more preferably 5 µm or less. Said filaments may have diameters greater than 1 µm, preferably greater than 2 µm. Preferably, values for the number average of said diameters of said particles in said product are also as stated above.

Particles of said filamentous fungus in said product may comprise filaments having an aspect ratio (length/diameter) of less than 1000, preferably less than 750, more preferably less than 500, especially of 250 or less. The aspect ratio may be greater than 10, preferably greater than 40, more preferably greater than 70. Preferably, values for the average aspect ratio of said particles (i.e. the average of the lengths of the particles divided by the average of the diameters of the particles) in said product are also as stated above.

Said product preferably comprises mycoprotein paste as herein described. Said product preferably comprises, on a dry matter basis, at least 15 wt %, preferably at least 19 wt %, more preferably at least 21 wt % of filamentous fungus (preferably of the type described in the definition of the mycoprotein paste hereinafter described).

Said product preferably comprises less than 30 wt %, preferably less than 28 wt %, more preferably less than 26 wt % of said filamentous fungus, on a dry matter basis.

Said product suitably includes 85 wt % or less, preferably 81 wt % or less, more preferably 79 wt % or less of water. Said product may include at least 70 wt %, preferably at least 72 wt %, more preferably at least 74 wt % water.

In said product, the sum of the wt % of water and filamentous fungus (e.g. mycoprotein as described) is suitably at least 95 wt %, preferably at least 98 wt %, more preferably at least 99 wt %, especially at least 99.5 wt %.

Said product may have a weight of at least 0.10 g, preferably at least 0.18 g. The weight may be less than 3.0 g, preferably less than 2.5 g.

The invention extends to a collocation comprising a multiplicity, for example at least 50, at least 500 or at least 5000 of said products. Said collocation may comprise a receptacle including said multiplicity of products.

The sum of the weights of the products in the collocation may be at least 1 kg, for example at least 5 kg. It may be less than 50 kg or less than 25 kg.

For the products in the collocation, the average Dimension (A) is suitably at least 3 mm, is preferably at least 4 mm, is more preferably at least 5 mm and, especially, is at least 6 mm. It may be less than 13 mm, suitably less than 12 mm, preferably less than 10 mm, more preferably less than 9 mm, especially 8 mm or less.

For the products in the collocation, the average Dimension (B) is suitably at least 12 mm, is preferably at least 14 mm, is more preferably at least 16 mm and, especially, is at least 18 mm. It may be less than 40 mm, suitably less than 30 mm, preferably less than 28 mm, more preferably less than 26 mm, especially 23 mm or less.

The average weight of products in the collocation may be at least 0.10 g, preferably at least 0.18 g. The average weight may be less than 3.0 g, preferably less than 2.5 g.

According to a second aspect of the invention, there is provided a method of making a product according to the first aspect, the method comprising:
(i) selecting a mass of filamentous fungus;
(ii) treating said mass to define a product having dimensions (A) and (B) as described in said first aspect.

The method preferably includes a step of freezing the mass to define a frozen product as described in the first aspect.

Freezing to define a frozen product preferably does not include use of any cryogenic freezing means.

Freezing preferably does not involve use of a liquefied gas. In the method, the minimum temperature the mass of filamentous fungus and/or said product is subjected to is preferably greater than −50° C., for example greater than −25° C.

Freezing of said mass and/or said product preferably comprises a mechanical freezing process.

Freezing may involve use of a cooling fluid, for example, cold air, at a temperature of greater than −30° C., for example greater than −25° C. or greater than −22° C.

In the method said product may be contacted with said cooling fluid for a period of less than 30 minutes, preferably less than 25 minutes, more preferably less than 20 minutes, especially less than 15 minutes or even less than 12 minutes. Contact may be for at least 5 minutes, at least 7 minutes or at least 9 minutes.

The method may comprise extruding the mass of material to define an extrudate (e.g. in the form of a rope) which is suitably directed onto a moving belt. The belt is suitably movable in a housing in which said cooling fluid flows. The rope is suitably conveyed by the belt and frozen during such conveyance. Downstream, the method comprises fragmenting the extrudate to define a product (suitably a multiplicity of products as described herein). Fragmentation may involve cutting the product; or the product may be fragmented by falling form a height onto a surface so that impact with the surface causes fragmentation of the product which is suitably in a frozen, brittle state prior to impact.

The method may comprise storing the product for at least 4.5 months, preferably at least 6 months, more preferably at least 9 months, especially at least 1 year or even at least 1.5 years in a frozen state.

According to a third aspect of the invention, there is provided a method of making a foodstuff, the method comprising:
  (i) selecting a product (preferably a collocation comprising a multiplicity of products) as described in the first or second aspect; and
  (ii) contacting said product, either before or after some processing thereof, with one or more other ingredients which are to be included in the foodstuff.

Said product selected in step (i) may be in a frozen state, for example as described in accordance with said first and/or second aspects. Said product is preferably defrosted prior to step (ii) of the method. Said product may be at a temperature of at least 1° C., at least 5° C. or at least 10° C. prior to step (ii).

In the method, said product is preferably treated to disperse the filamentous fungus.

Advantageously, it is found that, by using the method described, a homogenous foodstuff can readily be prepared on an industrial scale, even after very long term storage of products, by mixing said products with other ingredients.

Suitably, prior to said product being defrosted, it is stored. It is preferably stored in a frozen state, for example at a storage temperature of less than −10° C., preferably less than −15° C., more preferably less than −18° C. Said storage temperature may be greater than −30° C., for example greater than −25° C. Said storage temperature may be in the range −17° C. to −22° C.

Said product may be stored, for example at a said storage temperature as described, for a period of at least 3 months, preferably at least 5 months, more preferably at least 9 months. In some cases, said product may be stored, for example at a said storage temperature as described, for at least 1 year, at least 1½ years or at least 2 years. Advantageously, it is found that the product described can be stored for very long periods, for example at a said storage temperature as described, whilst maintaining important characteristics of the filamentous fungus, for example relative ease of dispersion using industrial mixing equipment and consumer acceptability of foodstuffs made using such a filamentous fungus. Suitably the mass of material is stored for 6 months to 3 years, for example 1 year to 3 years or 1 year to 2½ years, in a frozen state, suitably at a temperature in the range −17° C. to −22° C., prior to being defrosted.

After storage, for example at a temperature and for a time period as described, said multiplicity of products may be defrosted. They are suitably defrosted at a temperature of at least 1° C. They may be defrosted at a temperature of at least 2° C. They may be defrosted so they attain a temperature of less than 20° C., preferably 10° C. or less. They are preferably defrosted and maintained at a temperature in the range 2° C. to 10° C.

Step (ii) of the method suitably comprises dispersing a multiplicity of said products with said one or more other ingredients. Advantageously, it is found that, even after very long term storage as described, said multiplicity of products can readily be dispersed using industrial mixing equipment. This is in contrast to the dispersibility of a mass of filamentous fungus, frozen by an alternative method to that described.

In step (ii) of the method, said multiplicity of products may be at a temperature of at least 2° C. immediately prior to said contact. The temperature may be less than 20° C. or 10° C. or less.

In step (ii), said multiplicity of products contacted with said one or more other ingredients may include 30 to 95 wt % of filamentous fungus on a wet matter basis. The method may comprise selecting at least 70 wt %, preferably at least 80 wt %, more preferably at least 90 wt % of said filamentous fungus (e.g. mycoprotein paste as herein defined) on a wet matter basis and contacting said filamentous fungus with said other ingredients, suitably up to 100 wt %.

Said one or more ingredients referred to in step (ii) may include an edible hydrocolloid. The total amount of edible hydrocolloid(s) included in said foodstuff may be at least 0.5 wt %, for example at least 1 wt %. The total amount may be less than 10 wt %, preferably less than 5 wt % or less than 3 wt %.

Said one or more ingredients referred to in step (ii) may include egg albumin. For example, said foodstuff prepared may include 0.1 to 5 wt %, for example 0.2 to 4 wt % of egg albumin.

Said one or more ingredients referred to in step (ii) may include one or more flavourants. The total amount of flavourant(s) in said foodstuff may be at least 0.2 wt %, preferably at least 1 wt %. The total amount may be less than 5 wt % or less than 3 wt %.

The total amount of water in said foodstuff prepared in the method may be at least 25 wt %, preferably at least 30 wt %, more preferably at least 50 wt %, especially at least 70 wt %. The total amount of water may be less than 81 wt %. The total amount of water in said foodstuff prepared in the method may be in the range 25 to 81 wt %, preferably in the range 50 to 81 wt %, more preferably in the range 60 to 80 wt %.

Said foodstuff may include:
  10 to 35 wt % (preferably 12 to 30 wt %) of said filamentous fungus on a dry matter basis;
  40 to 85 wt % (preferably 50 to 85 wt %) of water; and
  1 to 20% (preferably 3 to 20 wt %) of said one or more other ingredients.

In said foodstuff, a ratio (BB) defined as the weight of water divided by the weight of filamentous fungus on a dry matter basis, may be at least 2, preferably at least 3. Ratio (BB) may be less than 6, preferably less than 5, more preferably less than 4.5.

After contact as described in step (ii) of the method, and preferably after dispersing of said filamentous fungus, a substantially homogenous material is suitably produced comprising said dispersed filamentous fungus and said one or more other ingredients. Said substantially homogenous mass may be cooked, for example to cause rheological changes, for example setting of egg albumin or other hydrocolloids (when included). Subsequently, said substantially homogenous material may, in a step (iii), be subjected to a reduced temperature of less than 0° C., preferably less than −4° C., more preferably less than −15°. It may be subjected to a temperature in the range −4° C. to −25° C., for example in the range −15° C. to −25° C. As a result, said substantially homogenous material may be frozen. This step is suitably a freeze texturization step as referenced herein.

Any feature of any aspect of any invention described herein may be combined with any feature of any other aspect of any invention described herein mutatis mutandis.

WORKING EXAMPLES

The following material is referred to hereinafter:

Mycoprotein paste—Mycoprotein paste-refers to a viscoelastic material comprising a mass of edible filamentous fungus derived from *Fusarium venenatum* A3/5 (formerly classified as *Fusarium graminearum* Schwabe) (IMI 145425; ATCC PTA-2684 deposited with the American type Culture Collection, 12301 Parklawn Drive, Rockville Md. 20852) and treated to reduce its RNA content to less than 2% by weight by heat treatment. Further details on the material are provided in WO96/21362 and WO95/23843. The material may be obtained from Marlow Foods Limited of Stokesley, U. K. It comprises about 23-25 wt % solids (the balance being water) made up of non-viable RNA reduced fungal hyphae of approximately 400-750 μm length, 3-5 μm in diameter and a branching frequency of 2-3 tips per hyphal length.

In the Examples which follow, Example 1 describes freezing of discs in a first freezing process; Example 2 includes an alternative freezing method; Examples 3 to 6 describe long-term storage and subsequent defrosting of products; Examples 7, 8 and 10 describe assessments made on products; and Example 9 describes the preparation of a foodstuff.

Example 1—Freezing of Mycoprotein Paste (First Freezing Process)

Figure 2:
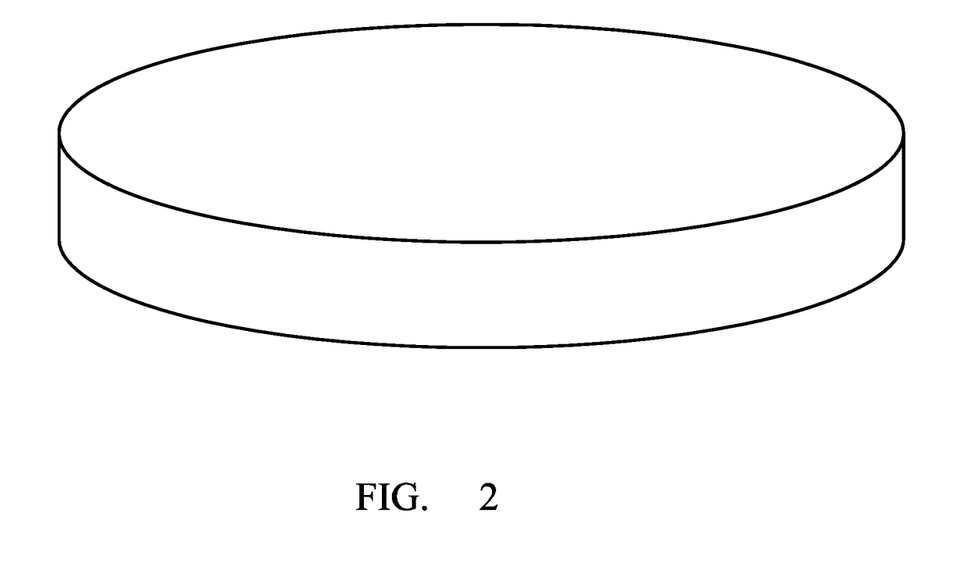
FIG. 2 is a representation of a disc of mycoprotein.

In the process, air blast freezing involves an air blast spiral freezer. In the process, a long, slow moving mesh belt passes through an enclosure containing very cold air in motion. The speed of the belt is variable according to the time necessary to freeze the product which for expediency is in the form of discs, as represented in FIG. 2, with a weight of 40 g after freezing of mycoprotein paste. The cold air is introduced into the tunnel at the opposite end from the one where the product to be frozen enters; that is, the air flow is counter to the direction of passage of the product. The temperature of the air used is −21° and the product is within the freezer for about 45 minutes. This is sufficient to freeze the core of the product to a temperature of at least −18° C.

After freezing, the frozen discs are packed into 20 kg boxes and moved into a standard commercial cold store held at −18° C. to −21° C.

The above process is currently used commercially but the details described have not been published.

Example 2—Freezing of Mycoprotein Paste (Second Freezing Process)

Figure 3:
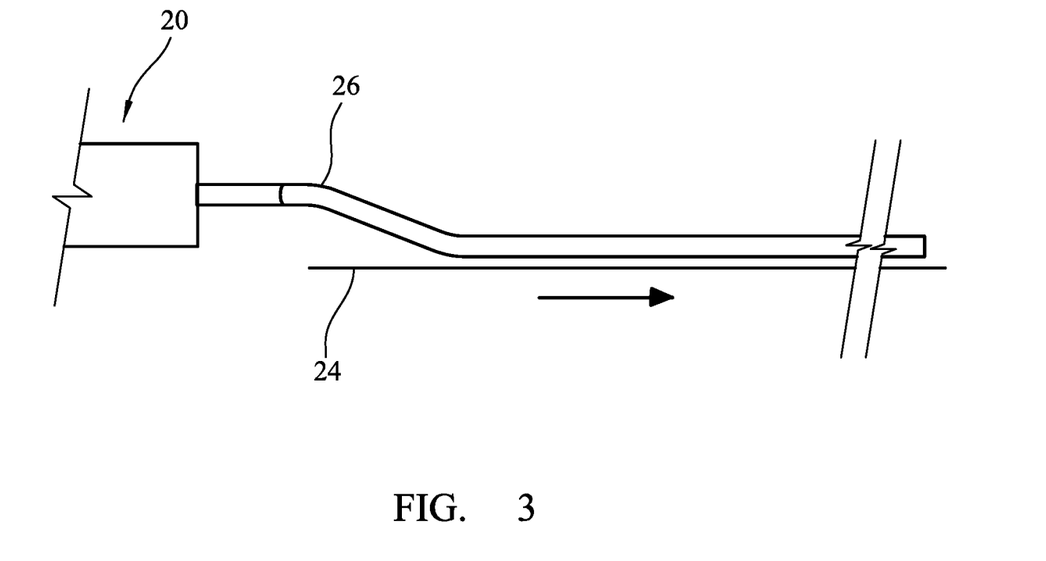
FIG. 3 is a representation of extrusion apparatus delivering an extruded rope of mycoprotein paste onto a moving belt which moves within an air blast freezer (not shown)

(a) Referring to FIG. 3, an extruder 20 for extruding mycoprotein via a circular cross-section nozzle is positioned adjacent a slow moving belt 24 of an air blast spiral freezer, identical to the freezer referred to in Example 1. Extrudate 26 (which is rope-like) passes from the nozzle and contacts the belt 24 which conveys it through the freezer. The temperature of the air in the freezer is at −21° C. and each part of the rope-like extrudate 26 has a residence time in the freezer of about 11 minutes. This is found to be sufficient to freeze the core of the rope to at least −18° C., as monitored by a suitably positioned temperature probe.

Figure 4:
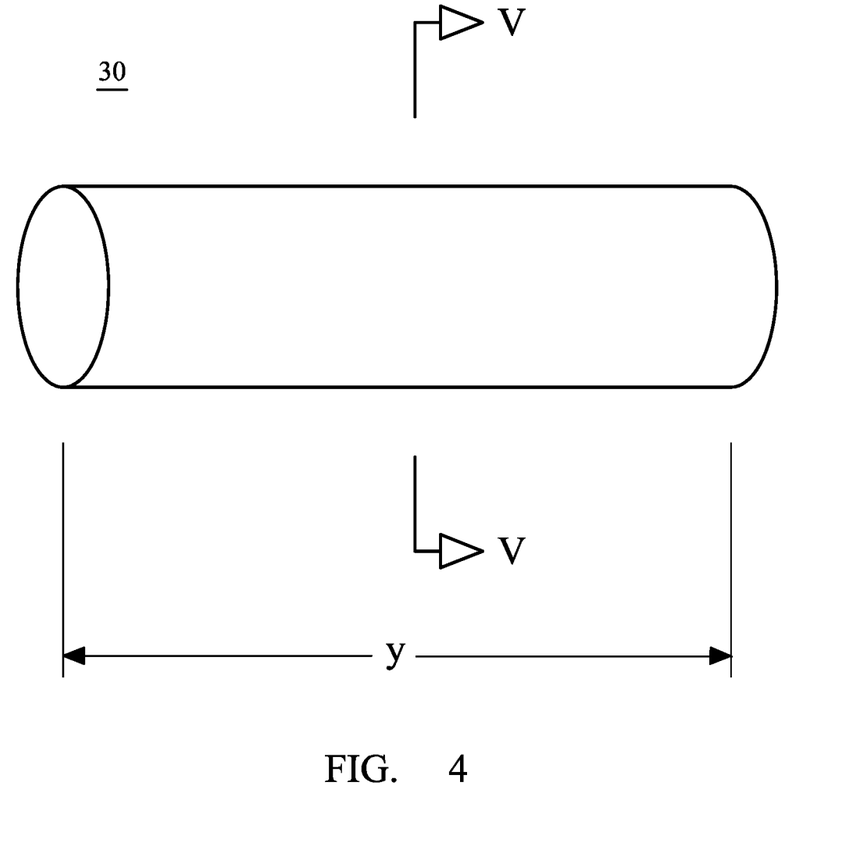
FIG. 4 is a representation of a rod of mycoprotein.
Figure 5:
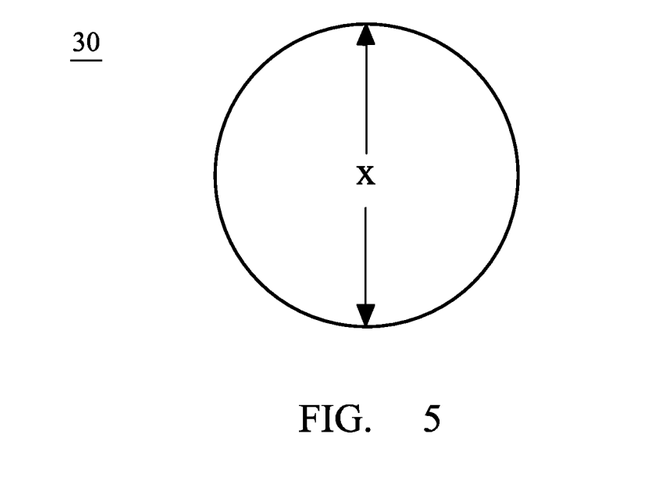
FIG. 5 is a cross-section along line V-V of FIG. 4.

On exiting the freezer, the rope-like extrudate 26 falls into a receptacle (not shown). Since at this stage the extrudate is brittle, it shatters on contact with the receptacle to form short pieces of frozen mycoprotein paste as represented in FIGS. 4 and 5. Referring to the figures, a rod 30 of frozen mycoprotein has a circular cross-section (FIG. 5) of diameter of 3 mm and an average length of about 30 mm. Rods which are collected in the receptacle after shattering of the rope have random lengths.

(b) In an alternative embodiment, rods may be manufactured having 10 mm diameter. In this case, a cutter may be provided downstream of the belt of the freezer and this may be arranged to slice the rope into predetermined, substantially constant lengths of 21 mm.

Example 3—Long Term Storage of Frozen Mycoprotein

After freezing as described in Examples 1 and 2, the products (discs or rods respectively) may be packed into boxes and placed in a standard commercial cold store held at −18° C. to −21° C., prior to use in formulating foodstuff comprising the mycoprotein and other ingredients. Subsequent defrosting of the mycoprotein discs or rods may be undertaken using one of the three processes described in Examples 4 to 6 below.

Example 4 Process—Defrost in Chiller

The frozen paste is placed in a chiller at 4° C. to 8° C. for at least two nights (ca. 40 hours) to bring the paste to the temperature of the chiller.

Example 5 Process—Defrost at Ambient Temperature

The frozen paste is placed in the ambient environment (approximately 20° C. for 2-3 hours) to bring the paste up to ambient temperature.

Example 6 Process—Defrost in Steamer

The frozen paste is placed in a kitchen commercial steamer for 3 minutes at 100° C.

The defrosted paste may be assessed as described in Examples 7 and 8.

Example 7—General Method for Assessing Defrosted Mycoprotein Paste Dispersibility To disperse the mycoprotein paste, discs are broken into four equal pieces before being placed in an 800 W Kenwood Chef (Trade Mark) mixer and mixed for one minute at speed 1.

Example 8—Backwards Extrusion Analysis of Defrosted Mycoprotein Paste

This test measures the consistency of viscous products. A test rig is comprised of a sample container which is centrally located beneath a disc plunger. The disc plunger performs a compression test which extrudes the product up and around the edge of the disc. Samples of paste can be assessed for 'firmness', 'consistency' and 'cohesiveness'.

The defrosted paste may be included as an ingredient in a foodstuff as described in Example 9.

Example 9—General Method for Preparation of Foodstuff

A foodstuff may be prepared by selecting mycoprotein paste which had been defrosted as described in Examples 4 to 6. The paste may be weighed into a mixing bowl of a domestic high speed kitchen mixer and water added, followed by mixing for 1 to 3 minutes. Then, the other, dry ingredients (for example, flavour, and egg albumen, may be added and mixed for several minutes. When an even mix has been produced, mixing is stopped and the mixed materials may be placed on grease-proof baking paper and formed into rectangular cross-section blocks of 15 mm thickness using a corresponding frame of a forming machine. The blocks may then be transferred into a steamer and cooked at 100° C. for about 20 minutes to set the egg albumen. After steaming, the blocks may be placed in a blast chiller for 15 minutes before being diced manually using a knife into the shape of meat pieces. The diced pieces may then be transferred to a blast freezer on a tray without any packaging, and left to freeze for around 60 minutes. The frozen pieces may then be freeze texturized by being transferred into a cold store and held at −21° C. for at least a week before defrosting for evaluation.

Preliminary results suggest the paste of Example 2 may be stored for many months (even years) longer than the paste of Example 1 whilst still performing like fresh paste when defrosted after long term storage and/or mixed with other ingredients to prepare a foodstuff for human consumption. Surprisingly, preliminary results suggest the paste will perform similarly to paste frozen cryogenically as described in co-pending application No. GB 1707876.7. Advantageously, however, capital and operation costs associated with the Example 2 method are far less than that of the cryogenic method described in the co-pending application. The invention is not restricted to the details of the foregoing embodiment(s).

Example 10—General Method for Determining Ice-Crystal Sizes in Frozen Mycoprotein Samples Using cryoSEM A small sample is cut from the centre of a frozen rod or disc and mounted using a 50/50 mixture of OCT and carbon conductive onto a cryoSEM shuttle. With the sample at ambient temperature (eg 19° C.), the shuttle including sample is frozen in liquid nitrogen slush (−210° C.). The shuttle is transferred under vacuum to a preparation chamber and left on the stage to equilibrate to −140° C.

The sample is fractured, then surface etched by warming to −80° C. for 5 mins then re-cooling to −140° C., before being coated with a few nm of gold/palladium and loading onto the SEM stage, also at −140° C. A Jeol JSM-6490LV SEM machine was used, with imaging being performed at 8 kV with a working distance of around 16 mm. A skilled person is aware how to adjust parameters to produce suitable images.

Example 11—Ice-Crystal Size Measurements

Using the method described in Example 10, the ice crystal sizes of a disc as described in Example 1 and rod as described in Example 2 were measured and the results are provided below.

| Product | Ice-crystal size |
|---|---|
| As per Example 1 | 20-140 μm |
| As per Example 2(a) | 2-4 μm |

The invention extends to any novel one, or any novel combination, of the features disclosed in this specification (including any accompanying claims, abstract and drawings), or to any novel one, or any novel combination, of the steps of any method or process so disclosed.

The invention claimed is:

1. A product comprising a filamentous fungus wherein the product has a dimension (A) measured in a first direction and a dimension (B) measured in a second direction, wherein dimension (A) is in the range 2 mm to 15 mm and dimension (B) is in the range 10 mm to 50 mm, wherein dimension (B) is greater than dimension (A); and wherein said product comprises at least 15 wt % of filamentous fungus on a dry matter basis and, wherein, in said product, the sum of the wt % of water and filamentous fungus on a dry matter basis is at least 95 wt %.

2. A product according to claim 1 wherein dimension (A) is at least 3 mm and is less than 13 mm.

3. A product according to claim 1, wherein dimension (B) is at least 12 mm and is less than 40 mm.

4. A product according to claim 1, wherein said product is elongate and/or comprises an extrudate.

5. A product according to claim 1, wherein the cross-sectional shape of said product is substantially circular.

6. A product according to claim 1, wherein said product has a cross-sectional area of less than 175 mm$^2$.

7. A product according to claim 1, wherein said product has a ratio defined as the surface area (in mm$^2$) divided by the volume (in mm$^3$) of at least 0.3 mm$^{-1}$ and less than 5 mm$^{-1}$.

8. A product according to claim 1, wherein the aspect ratio of the product is defined as dimension (B) divided by dimension (A), wherein said aspect ratio is at least 1.2; and is less than 10.

9. A product according to claim 1, wherein said product is in a frozen state.

10. A product according to claim 1, wherein said filamentous fungus comprises a fungus selected from fungi imperfecti.

11. A product according to claim 1, wherein the level of RNA in the filamentous fungus is less than 2 wt % on a dry matter basis.

12. A product according to claim 1, wherein said product comprises less than 30 wt % of said filamentous fungus on a dry matter basis.

13. A product according to claim 1, wherein, in said product, the sum of the wt % of water and filamentous fungus on a dry matter basis is at least 99 wt %.

14. A product according to claim 1, wherein said product has a weight of at least 0.10 g; and a weight of less than 3.0 g.

15. A product according to claim 1, which includes ice crystals having an ice-crystal size within the product of less than 20.0 μm.

16. A product according to claim 1,
wherein dimension (A) is at least 6 mm and is less than 13 mm;
wherein dimension (B) is at least 18 mm and is less than 40 mm;
wherein said product is elongate;

wherein the cross-sectional shape of said product is substantially circular;

wherein said product has a ratio defined as the surface area (in mm$^2$) divided by the volume (in mm$^3$) of at least 0.4 mm$^{-1}$); and less than 5 mm$^{-1}$;

wherein the aspect ratio of the product is defined as dimension (B) divided by dimension (A), wherein said aspect ratio is at least 1.2; and is less than 10;

wherein said product is in a frozen state; and wherein said filamentous fungus comprises a fungus selected from fungi imperfecti.

17. A product according to claim 1, wherein dimension (A) is at least 6 mm and is less than 13 mm;

wherein dimension (B) is at least 18 mm and is less than 40 mm;

wherein said product has a ratio defined as the surface area (in mm$^2$) divided by the volume (in mm$^3$) of at least 0.4 mm$^{-1}$) and less than 5 mm$^{-1}$;

wherein the aspect ratio of the product is defined as dimension (B) divided by dimension (A), wherein said aspect ratio is at least 1.2 and is less than 10; and wherein said product is in the form of a disc or rod.

18. A product according to claim 16, wherein said product has a weight of at least 0.18 g and a weight of less than 3.0 g.

19. A product according to claim 17, wherein said product has a weight of at least 0.18 g and a weight of less than 3.0 g.

20. A product according to claim 19, wherein the sum of the wt % of water and filamentous fungus on a dry matter basis is at least 99 wt %.

* * * * *